United States Patent [19]
Sashin et al.

[11] Patent Number: 4,696,022
[45] Date of Patent: Sep. 22, 1987

[54] STEREOSCOPIC RADIOGRAPHY APPARATUS AND METHOD

[75] Inventors: Donald Sashin, Pittsburgh, Pa.; Ernest J. Sternglass, Bloomington, Ind.

[73] Assignee: University of Pittsburgh, Pittsburgh, Pa.

[21] Appl. No.: 574,588

[22] Filed: Jan. 27, 1984

[51] Int. Cl.⁴ ............................................. A61B 6/02
[52] U.S. Cl. ................................. 378/41; 250/363 S
[58] Field of Search ........................... 378/41, 42, 99; 358/111; 350/96.27; 250/363 S

[56] References Cited

U.S. PATENT DOCUMENTS

| | | | |
|---|---|---|---|
| 3,043,910 | 7/1962 | Hicks, Jr. | 350/96.27 |
| 3,058,021 | 10/1962 | Dunn | 358/111 |
| 3,432,657 | 3/1969 | Slavin | 378/41 |
| 3,767,931 | 10/1973 | Williams | 250/511 |
| 3,829,701 | 8/1974 | Hura | 250/511 |
| 3,866,047 | 2/1975 | Hounsfield | 250/360 |
| 3,934,151 | 1/1976 | Stowe et al. | 250/505 |
| 3,947,689 | 3/1976 | Wagner | 250/512 |
| 3,973,127 | 8/1976 | Matsuda et al. | 250/445 T |
| 4,010,371 | 3/1977 | Lemay | 250/366 |
| 4,029,964 | 6/1977 | Ashe | 250/368 |
| 4,149,082 | 4/1979 | Haendle et al. | 378/41 |
| 4,179,100 | 12/1979 | Sashin et al. | 250/416 TV |
| 4,214,267 | 7/1980 | Roese et al. | 378/111 |

OTHER PUBLICATIONS

"Self-Scanning Protodiode Arrays for Spectroscopy", Snow, Research-Development, Apr. 1976, pp. 18–22.
Stauffer et al, Radiology, 79, pp. 30–34 (1962).
An Introduction to the Physics of Diagnostic Radiology, E. E. Christensen, Ch. 19 (Lea & Febiger, Phila. 1978).
Kuroda et al, Electromedica (No. 1, pp. 22–27, 1/82.
Stauffer et al, Radiology, 82 pp. 125–126 (1964).

Primary Examiner—Janice A. Howell
Attorney, Agent, or Firm—Arnold B. Silverman

[57] ABSTRACT

Stereoscopic radiography apparatus includes a source of two beams of radiation, collimators so as to convert the beams into generally fan shaped beams, radiation detectors for converting the radiation passing through an object being examined into an electrical signal containing image information. The radiation detector may have at least one scintillator to convert radiation which has passed through an object into light, and at least one self-scanning array of photodiodes to convert the light into an electrical signal containing image information. Fiber optic coupling may be provided between the scintillator and the self-scanning array of photodiodes. The first image information resulting from the first beam and second image information resulting from a second beam are created substantially simultaneously. Apparatus for receiving the signal to store, process or display the image may be provided along with a visual display system. In one embodiment the two radiation beams are emitted simultaneously and in another embodiment they are emitted sequentially. A uniquely configured fiber optic coupling member may be employed. The method of effecting such stereoscopic radiographic imaging.

27 Claims, 12 Drawing Figures

STEREOSCOPIC RADIOGRAPHY APPARATUS AND METHOD

BACKGROUND OF THE INVENTION

1. Field of the Invention

This invention relates to stereoscopic radiography apparatus and an associated method and, more specifically, it relates to an efficient system for rapidly obtaining high resolution images even when the object being imaged is moving.

2. Description of the Prior Art

The advantageous use of radiation, such as X-rays, gamma rays and nuclear particles has long been known in medical, industrial and other environments. A wide variety of systems and procedures have been employed in such uses depending, in part, upon safety considerations, the nature of the object to be imaged and equipment limitations. See generally U.S. Pat. Nos. 3,767,931; 3,829,701; 3,866,047; 3,934,151; 3,947,689 and 3,973,127. Various forms of photodetectors, such as photomultipliers have been known in such systems. See generally U.S. Pat. Nos. 4,010,371 and 4,029,964. It has also been known to use self-scanning photodiode arrays for spectroscopy (Snow, Research-Development, April 1976) and for medical and non-medical units (see U.S. Pat. No. 4,179,100 the disclosure of which is hereby expressly incorporated herein by reference).

It has also been known to provide systems wherein collimated radiation is permitted to pass through an object and impinge upon a scintillator screen with fiber optic coupling means transporting the light to one or more arrays of self-scanning photodiodes which emit a responsive electrical signal which may then be computer enhanced or otherwise processed or imaged. See U.S. Pat. No. 4,179,100.

Various suggestions regarding stereoscopic imaging used in connection with X-ray radiation have been made, but none has been provided which permits very rapid imaging so as to be adapted to be effective with rapidly moving members. See generally, An Introduction to the Physics of Diagnostic Radiology, by E. E. Christensen et al. chapter 19, (Lea and Debigo, Philadelphia, 1978); Kuroda et al., *Electromedica* (no. 1, pp. 22–27, 1/82; Stauffer et al., *Radiology*, 82 pp. 125–126 (1964) and Stauffer et al., *Radiology*, 79, pp. 30–34 (1962).

In spite of these prior disclosures, there remains a need for an effective means for high speed stereoscopic radiographic imaging.

SUMMARY OF THE INVENTION

The apparatus of the present invention in a preferred embodiment has met the above-described need by providing stereoscopic radiography apparatus employing two radiation beams which eminate from radiation source means and after collimation to achieve generally fan shaped beams are passed through an object. Radiation detector means receive radiation which has passed through the object being visualized and convert the radiation into responsive electrical signals. A form of detector means includes scintillator means which are optically coupled to a self-scanning array of photodiodes by fiber optic coupling means. Signal receiving means are operatively associated with the at least one array of photodiodes to store, process or display the image information.

In one embodiment, the beams are rapidly alternated with the radiation passing through the object being received by the same scintillator means and the same photodiode means. In another embodiment, the beams are on simultaneously and are each received by separate scintillator means associated with separate arrays of photodiodes.

A unique fiber optic coupler is also provided. The fiber optic coupler has a pair of sidewalls, a light receiving end wall and a light discharging end wall. The light discharging end wall is preferably shorter and of lesser area than the light receiving end wall. The fibers are preferably of a number of different lengths. This permits a large area of radiation receipt to correspond to a small area of photodiode array.

It is an object of the present invention to provide stereoscopic radiography apparatus which is adapted to operate very rapidly.

It is a further object of the present invention to provide stereoscopic radiography apparatus and an associated method which will preserve image quality.

It is another object of the present invention to provide a stereoscopic radiography system which has high contrast sensitivity and high spatial resolution.

It is another object of the invention to provide stereoscopic radiography apparatus which is adapted for digital computer processing to enhance the image.

It is a further object of the present invention to provide such a system wherein a unique fiber optic coupler may advantageously be employed.

It is a further object of the invention to provide a system capable of obtaining two views of the same region of the object being studied substantially simultaneously.

These and other objects of the invention will be more fully understood from the following description of the invention on reference to the illustrations appended hereto.

DESCRIPTION OF THE PREFERRED EMBODIMENTS

As used herein, the term "object" or "test object" or words of similar import will refer to various types of objects through which it is desired to pass radiation for test or diagnostic purposes including, but not limited to, humans and animals, specimens removed from humans and animals, non-destructive testing and security purposes. While for purposes of clarity of description specific reference will be made herein to a preferred use in medical environments, it will be appreciated that other forms of objects may be employed in connection with the apparatus of this invention in addition to medical uses and such other uses are expressly contemplated.

As used herein, the terms "self-scanning array of photodiodes", "self-scanning integrated array of photodiodes" and words of similar import shall mean one or more integrated circuit elements having a plurality of photodiodes, each associated with a storage capacitor on which it integrates electrical charges and a multiplex switch for periodic readout by means of an integrated switch register scanning circuit. This term shall expressly include, but not be limited to, linear arrays having about 60 to 4096 (preferably about 256 to 4096) photodiodes per integrated circuit and the associated circuitry, as well as planar or rectangular arrays of photodiodes. These arrays may have about 70 photodiodes per linear millimeter of array, for example.

As used herein, the term "image information" shall refer to the electrical signals emerging from the photodiode array, images or data created by use of said electrical signals, with or without intervening storage or modification thereof and images created with or without addition to or substraction from the image data.

As used herein in connection with a reference to a first radiation beam impinging on an object as related to the timing of a second radiation beam impinging upon the object, the term "substantially simultaneous" shall mean either having both beams concurrently operating or having the second beam turned on within less than about 10 milliseconds of turning off of the first beam.

Figure 1:
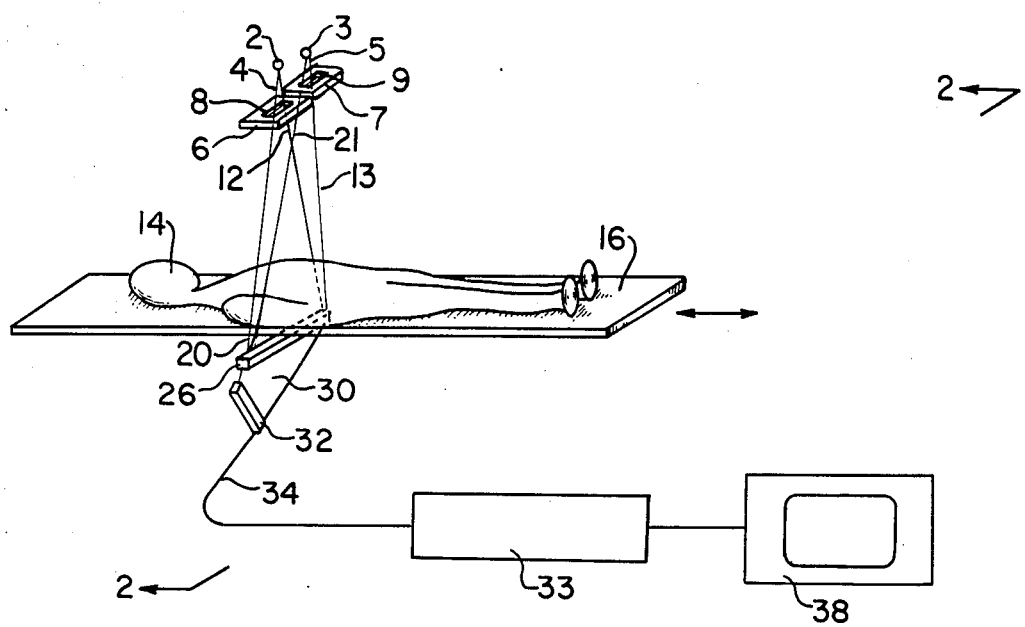
FIG. 1 is a schematic illustration of a form of stereoscopic radiography system of the present invention.
Figure 2:
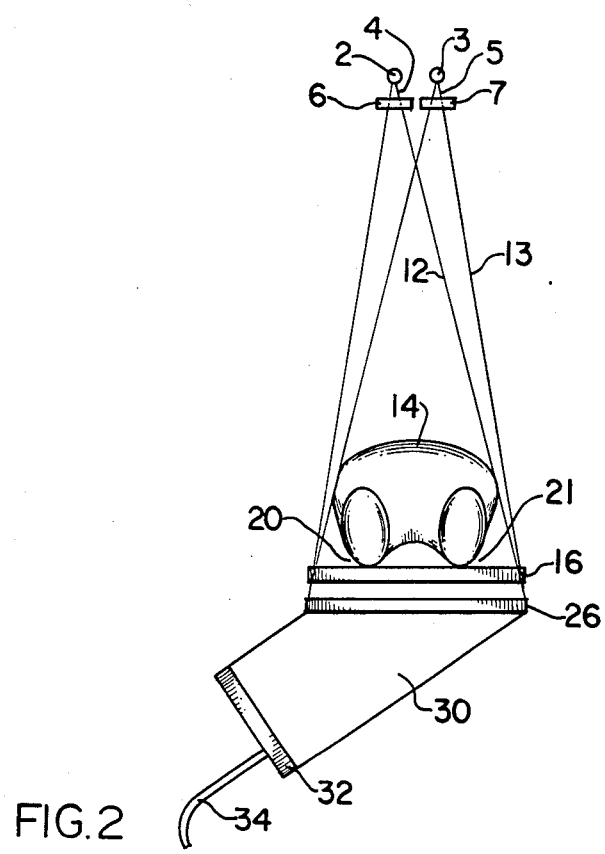
FIG. 2 is a cross-sectional illustration of the apparatus of FIG. 1 taken through 2—2.
Figure 3:
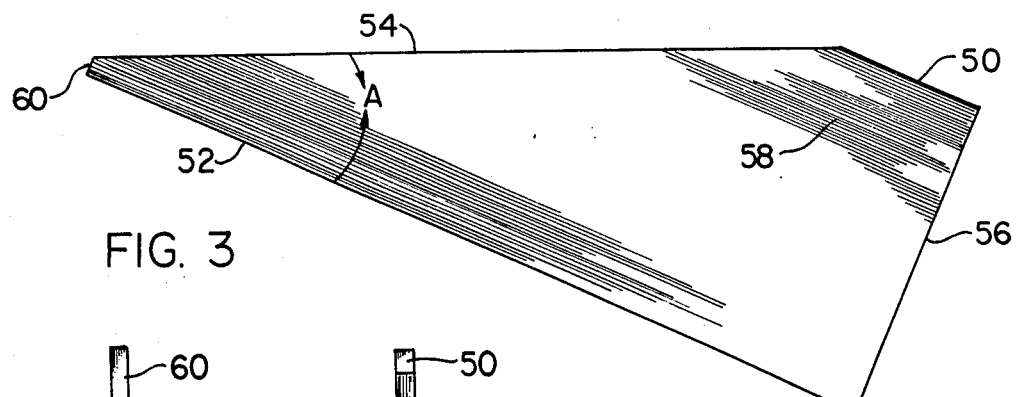
FIG. 3 is a front elevational view of a form of optic coupler of the present invention.
Figure 4:
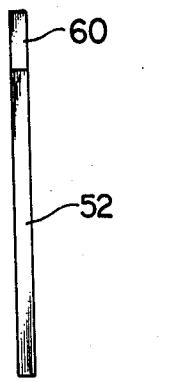
FIG. 4 is a right side elevational view of the optical coupler of FIG. 3.
Figure 5:
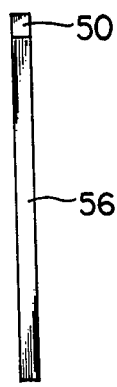
FIG. 5 is a left side elevational view of the coupler of FIG. 3.
Figure 6:
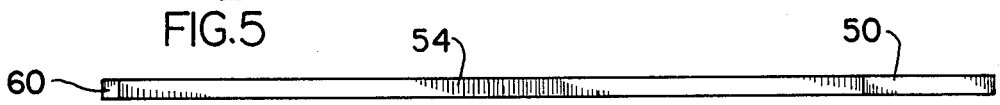
FIG. 6 is a top plan view of the coupler of FIG. 3.

Referring now more specifically to FIGS. 1 and 2 there is shown a pair of radiation sources 2, 3 which, in the form shown, are X-ray generators. It will be appreciated that other sources of radiation such as gamma-rays, for example, may be employed. These two sources 2, 3 may conveniently be separate X-ray tubes or a dual anode X-ray tube, for example. X-ray beams 4, 5 respectively, are emitted by radiation sources 2, 3. Collimators 6, 7 are positioned in the path of the beams, respectively, 4, 5. Each collimator 6, 7 has an associated slit 8, 9 which converts the generally conical X-ray beam 4, 5 into a generally flat fan shaped beam 12, 13.

In the form illustrated, the object to be subjected to the radiography is a patient 14 shown reclining on a moveable support table 16 which is adapted to be reciprocated in the directions indicated by the arrows. This movement of the support table 16 with respect to the rest of the radiography apparatus permits sequential exposure of various portions of the patient to the fan-shaped X-ray beams 12, 13. Alternatively, if desired, the patient can remain stationary and the rest of apparatus may be moved relative to the patient in order to achieve the same objective. The portions of the beams 12, 13 which have passed through the patient 14 are indicated generally by the numbers 20, 21.

Underlying the table 16 and receiving the radiation 20, 21 from each beam 12, 13 passing through the patient 14 is the radiation detector which, in the form illustrated includes scintillator means 26 and self-scanning photodiode array 32. The scintillator means 26, which may be a relatively narrow phosphor screen, converts the X-ray energy into visible light photons. For certain systems, such as in cases where low KVP is employed and silicon or germanium diodes are used with low intensity radiation, the radiation may be allowed to impinge directly on the diodes without the use of separate scintillator means.

Also, if desired, fiber optic means which serve to deliver light emitted by the scintillator means may contain the scintillator means or the scintillator means could be in the form of closely packed fibers of fluorescing glass provided in bundles.

Positioned in face-to-face adjacency with the scintillator means 26 is the fiber optic coupler 30 which is adapted to transport light from the scintillator means to the self-scanning array of photodiodes 32. The self-scanning linear array of photodiodes 32 emits electrical signals which correspond to the light which impinges thereon. The electrical signals, which contain image information, are then delivered to the electrical processing unit 33 by means of electrical wire 34. In a preferred embodiment, the electrical processing unit 33 may consist of a digital computer which receives electrical signals in a memory bank and then, with or without modification thereof, presents the desired image in desired output form such as by presenting a visual image, a stored image or a computer printout of the data. In the form shown in FIG. 1, the image is presented on cathode-ray tube 38, but it may be displayed on any other suitable display means.

It is preferred that the X-ray sources 2, 3 be spaced from each other a distance equal to about 1 to 4 inches. It is noted that this embodiment places photodiodes 32 out of the path of the X-ray beam.

It has long been known that it is difficult to produce stereoscopic images where there is rapid motion, such as a rapidly moving heart or the flow of blood in vessels such as occurs in angiography of the coronary arteries. The present invention overcomes problems inherent in such needs by obtaining two stereoscopic images of rapidly moving or changing systems, either within a few milliseconds of each other or simultaneously while preserving image quality and allowing digital enhancement for improved visualization.

The apparatus shown in FIGS. 1 and 2 provides use of high detailed line-scanning of the image in such a way as to produce two separate substantially simultaneously generated stereoscopic views of the object as distinguished from two separate views scanned in their entirety in sequence. As each line can be scanned in a few milliseconds or less, motion is effectively frozen and maximum detail is obtained in the two stereoscopic images that are recorded line-by-line a few milliseconds apart.

In the embodiment shown in FIGS. 1 and 2, the two beams share the same detector systems and are, therefore, energized alternately. In operation, each X-ray source 2, 3 will be energized for about 2 to 4 milliseconds after which it will be turned off and the other source will immediately be energized for a like period. The single line of one of the two required images which is generated during the period when each source 2, 3 is on will then be digitally recorded using known amplifiers and analog-digital converters which form a portion of the signal receiving means 33 along with the computer. This alternating process is repeated line-by-line until two complete sets of images are produced by way of the two X-ray sources.

The resultant recorded stereo image may then be viewed on a cathode-ray tube 38 or television monitor or other suitable means for examination in a number of possible ways. The view may be observed, for example, with electronically gated glasses which may be gated alternately employing crossed polarized glasses and a gated quarter-wave plate. Alternately, the image may be produced in two different colors such as red and green and may be viewed with suitably colored glasses wherein each lens will filter one color and permit the others to pass therethrough.

Referring to FIGS. 3 to 6, a preferred form of optical coupling means will be considered. The optical coupler has a pair of sidewalls 50, 52 which in the form shown are generally parallel to each other, a light receiving end wall 54 and a light discharging end wall 56. The individual fiber optics strands 58 are oriented generally parallel to the sidewalls 50, 52 and extend generally from end wall 54 to end wall 56. It will be appreciated that light received at end wall 54 will be transported by the fibers to end wall 56. In a typical installation the coupler may have a plurality of fiber strands having a diameter of about 5 to 10 micrometers. It is noted that the coupler in the form shown is of substantially uniform thickness. The angle A between sidewall 52 and end wall 54 is preferably about 20 to 45 degrees.

Continuing to refer to FIGS. 3 through 6, it is noted that as a result of the geometry the walls 50, 52, 54, 56 it will be appreciated that fibers of different lengths are provided in the optical coupler. If desired, the individual fibers may be tapered so as to converge toward wall 56.

In lieu of a plurality of individual fibers for optical coupling, one may employ a sheet of a suitable material (such as fiber glass, for example) having the desired properties.

As a result of the substantially uniform thickness of the optical coupler and the length of the light receiving end wall 54 being greater than the length of the light discharging end wall 56 it will be appreciated that the receiving end wall 54 may be substantially coextensive with scintillator means and yet have the light received from the scintillator 26 efficiently delivered to a relatively smaller self-scanning array of light emitting photodiodes 32. This results in a reduction in cost of the diode array required to convert light impinging on wall 54 into a corresponding electrical signal. It is preferred that the end walls 54, 56 each be generally planar so as to facilitate efficient coupling with respectively a scintillator 26 and the photodiode array 32. For convenience of manufacture, a flat surface 60 is shown as being interposed between walls 52, 54, but this may be ignored in determining angle A and the other characteristics described hereinbefore.

An alternate to the optical coupler of FIGS. 3 through 6 would be to be employ the twisted or tapered fibers disclosed in our prior U.S. Pat. No. 4,179,100.

Figure 7A:
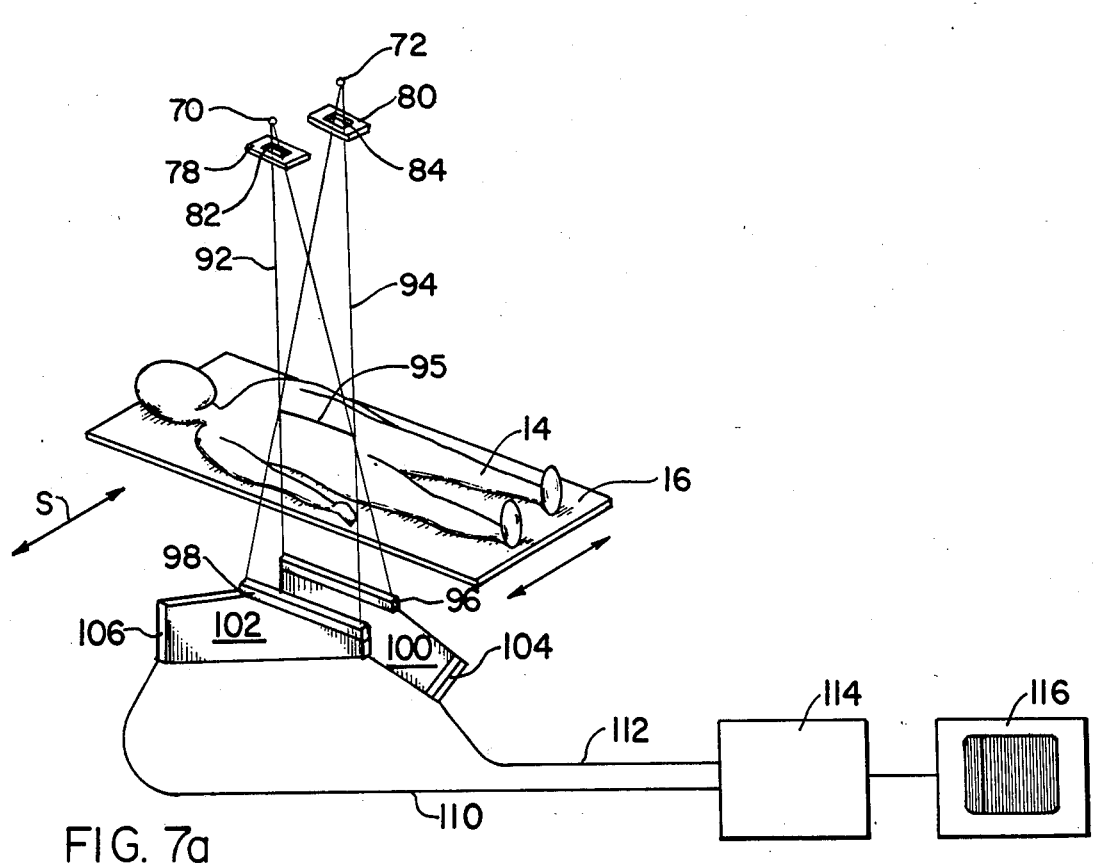
FIG. 7(a) is a schematic illustration, partially exploded, of another embodiment of the invention.

Referring to FIG. 7(a), an alternate embodiment of the invention which includes both X-ray generating systems being on at the same time and providing duplicate detection systems will now be considered. Radiation sources 70, 72 emit generally conical beams 74, 76, respectively, which are partially blocked by collimators 78, 80, respectively, which permit, through slots 82, 84 generally flat fan shaped beams 92, 94 to pass therethrough. While for clarity of illustration the radiation sources are shown as being spaced a substantial distance from each other, it is preferred that the spacing be about 1 to 4 inches. The patient 14 and support table 16 shown in FIG. 7(a) are subjected to relative movement to create a reciprocating scanning action in the direction indicated by double-headed arrow S. The portion of beams 92, 94 which pass through the object will be received, respectively, by scintillator means 96, 98. The radiation will be converted by the scintillator means 96, 98, such as a phosphor screen, into visible light which will be received, respectively, by fiber optic couplers 100, 102. While, for clarity of illustration the fiber optic couplers 100, 102 have been shown as being spaced from each other, it will generally be desirable to have them positioned sufficently close to each other as to be recording generally the same sector of the object, while not receiving undesired levels of stray radiation from the adjacent beam. Preferably, there should be a space of about 1 to 4 inches between the two fiber optic couplers 100, 102. The light discharged by coupler 100 will be received in photodiode array 104 and the light discharged by coupler 102 will be received in photodiode array 106. The photodiode arrays 104, 106 will transfer image information by wires 110, 112 to the signal receiving means 114 wherein suitable amplifier means, analog-digital convertor means and digital computer means may be provided for storing, recording and, if desired, modifying the image data. The image data may be visualized on cathode-ray tube 116, if desired.

Figure 7B:
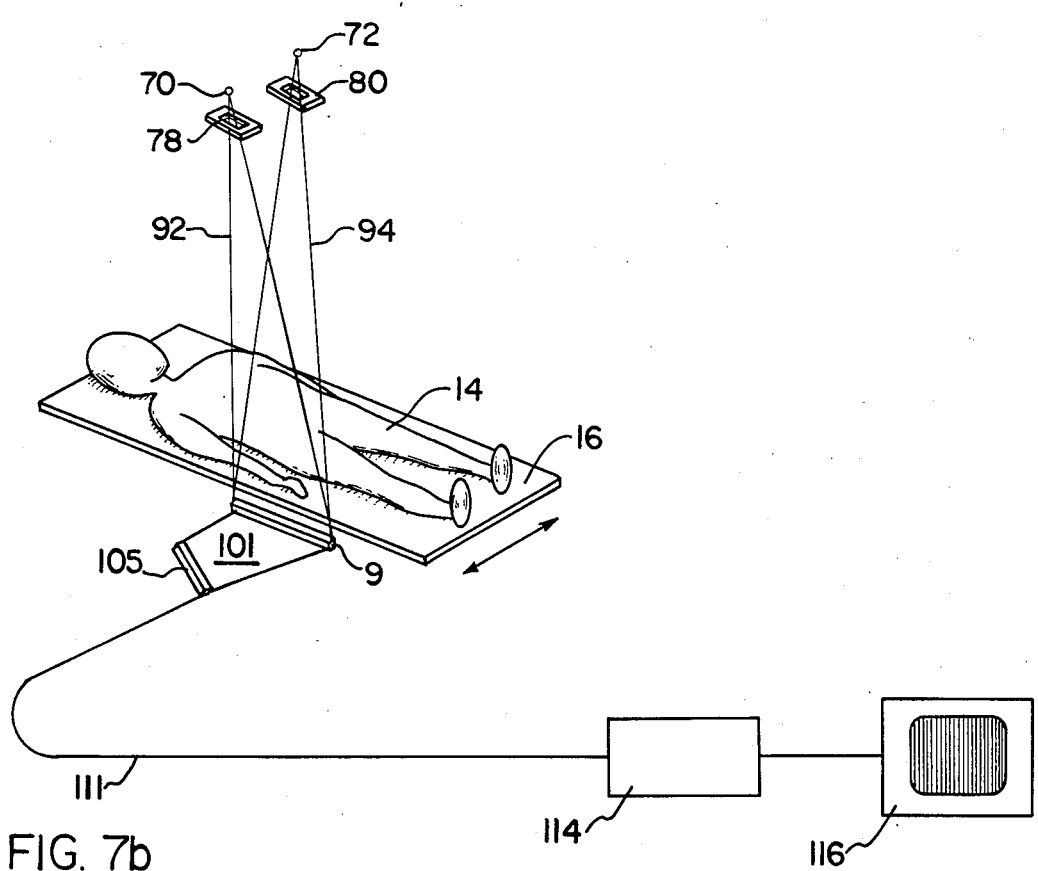
FIG. 7(b) is a schematic illustration of a further embodiment which is generally similar to FIG. 7(a)

FIG. 7(b) illustrates an embodiment similar to FIG. 7(a) except that as in the embodiment of FIGS. 1 and 2 a single detector system is employed and the two radiation beams are energized alternately. Scintillator means 97 alternately receives the portions of radiation beams 92, 94 which pass through patient 14 and converts the radiation to light which by fiber optic coupler 101 is delivered to diode array 105. The electrical signals emitted by diode array 105 is delivered by wire 111 to signal receiving means 114.

With this arrangement both X-ray generators 70, 72 may operate continuously and the individual images may be fed continuously to the signal receiving means 114. One of the advantages of this embodiment is that the heat loading efficiency of the X-ray tubes is improved so that more X-ray photons can be recorded and the image information quality thereby improved. One of the disadvantages of this embodiment is that the need to provide two independent detector systems increases the cost of the apparatus. As in the form shown in FIG. 7, the two X-ray beams cross on a common line 95 within the patient, they both visualize the same part of the patient, but from a slightly different angle with both views being recorded substantially simultaneously.

Figure 8:
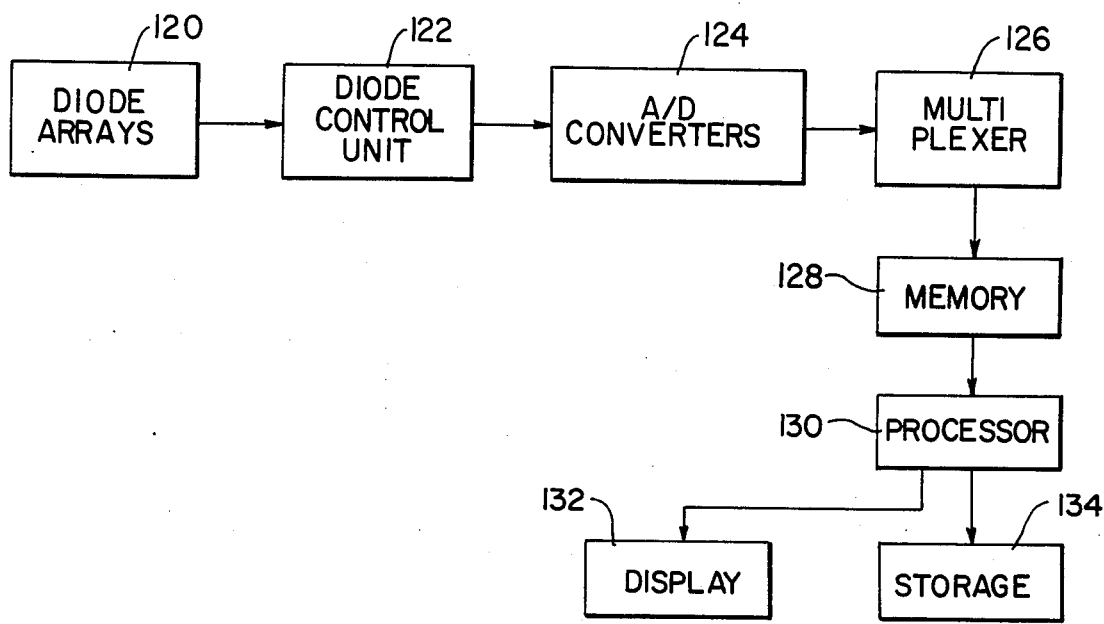
FIG. 8 is a block diagram of a form of data processing means of the present invention.

Referring to FIG. 8, a form of electrical processing means contemplated for use with the present invention will be considered. As the components and sequence of operations of these units are conventional and are well known to those skilled in the art a detailed explanation is not deemed necessary. The self-scanning photodiode arrays 120 detect the optical images from the scintillator by the optical coupler and convert the image into an electrical signal. The diodes are controlled by diode control unit 122 and the signal goes to the analog to digital convertor 124 which converts the analog signal to a digital signal. The process is controlled by a muliplex circuit 126 and the digital pulses go to the computer memory 128 for storage. The stored signals are digitally processed in the processor 130 and may be displayed on display 132 and/or may be stored for future use with storage device 134, such as magnetic disks or tapes, digital tape, storage tubes, digital computer memory, video tape, photographs or electron beam tape recorders. Also, if desired, a camera may be employed to photograph the image appearing on display 132.

Figure 9:
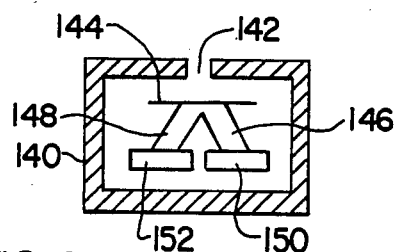
FIG. 9 is a cross-sectional illustration of a modified form of the self-scanning array of photodiodes and associated coupler.
Figure 10:
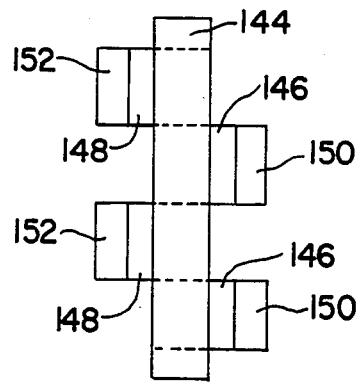
FIG. 10 is a top plan view of a portion of the photodiode array shown in FIG. 9.

Referring to FIGS. 9 and 10, a preferred form of self-scanning photodiode array for use in the present invention will be considered. In this embodiment, an enclosure 140 which is light radiation opaque is provided with an opening 142 into which the fan shaped beam of radiation which has passed through the object may pass. The scintillator 144 is in contact with a generally v-shaped fiber optic coupler which has a first series of legs 146 extending to one side and a second series of legs 148 extending to the other side. Associated with the fiber optics legs 146 are a series of self-scanning photodiode arrays 150. Associated with the fiber optic legs 148 are a series of self-scanning photodiode array 152. In operation, the X-ray will impinge upon the unitary scintillator strip 144 and will by the fiber optic means 146, 148 be delivered to the staggered arrays of self-scanning photodiodes 150, 152 with which the respective legs are associated. As is shown in FIG. 10, in this embodiment the self-scanning photodiode arrays 150, 152 are positioned in staggered fashion and are optically coupled to scintillator means 144 to provide continuous receipt of light emerging from the scintillator means by the arrays 150, 152. Alternate light pipes provide light to alternate photodiode arrays from alternate sections of the scintillator means 144. This embodiment provides unique means for minimizing the risk of undesired gaps in image information as displayed visually.

As an alternate to the preferred approach shown in FIGS. 9 and 10, precisely dimensioned self-scanning photodiode arrays may be placed in a linear close abutting relationship with direct fiber optic coupling so as to resist undesired gaps.

Figure 11:
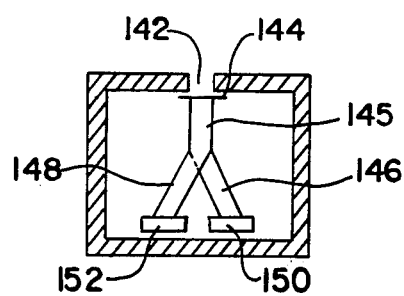
FIG. 11 is a cross-sectional illustration of a modified form of the staggered array shown in FIGS. 9 and 10.

FIG. 11 illustrates a modified form of staggered array which is generally similar to FIGS. 9 and 10 except that a series of alternating individual bent fiber optic couplers 145 which have a first series of legs 146 extending to one side and a second series of legs 148 extending to the other side. Associated with the fiber optic legs 146 are a series of self-scanning photodiode arrays 150. Associated with the fiber optic legs 148 are a series of self-scanning photodiode arrays 152. The best fiber optic couplers deliver the light from the scintillator means 144, respectively, to photodiode array 152, 150.

It will be appreciated, therefore, that the present invention provides an effective means for obtaining rapid stereoscopic images in an efficient and economical fashion. By providing substantially simultaneous radiation exposure in a line-by-line fashion movement of the portion of the object being subjected to radiography is arrested and high quality images are obtained. As the present invention facilitates use of narrow line detectors, most scattered radiation will miss the detector thereby preserving the image contrast without the need for Bucky grids.

While for purposes of illustration collimators with a single slit have been emphasized herein, it will be appreciated that if desired more than one slit in a given collimator or a single collimator having a slit for each beam may be provided if desired.

While specific reference has been made to a radiation source providing X-rays or gamma-rays, the invention is not so limited, and other forms of radiation such as particulate radiation including protons and mesons, for example, may be employed. In connection with particulate radiation as well as other forms, a generally rectangular beam having parallel sides may be used in lieu of a fan beam.

While for simplicity of disclosure reference has been made herein to the preferred use of self-scanning arrays of photodiodes as the preferred means of detecting radiation passing through the object being tested in stereoscopic imaging, it will be appreciated that the invention is not so limited. For example, other forms of solid-state diode arrays may be employed. A general reference herein to "radiation detectors" shall be deemed to encompass these types of detectors as well as other means of converting radiation into responsive electrical signals. With respect to diode arrays, single linear arrays, multiple linear arrays, staggered arrays, arrays disposed generally in a single plane ("planar arrays") or other suitable patterns may be employed.

While for purposes of simplicity of description herein, in general, examples showing a vertically oriented radiation beam have been employed it will be appreciated that the radiation may be directed from any desired angle or angles and also the patient or object may be oriented or moved vertically or angularly with respect to the floor of the room.

Whereas particular embodiments of the invention have been described above for purposes of illustration, it will be evident to those skilled in the art that numerous variations of the details may be made without departing from the invention as defined in the appended claims.

We claim:

1. Stereoscopic radiography apparatus comprising
    radiation source means for generating substantially simultaneously a first radiation beam and a second radiation beam,
    collimator means interposed between said radiation source means and an object to be exposed to radiation for converting said first and said second radiation beams into generally fan-shaped beams,
    radiation detector means disposed on the opposite side of said object from said radiation source means for converting the portion of said first and second radiation beams passing through said object into responsive electrical signals, containing first image information from said first beams and second image information from said second beams, and
    signal receiving means operatively associated with said radiation detector means to store, process or display said image information
    said radiation detector means includes scintillator means and an array of solid-state detector means,
    said scintillator means adapted to convert said radiation into light,
    said array of solid-state detector means adapted to receive said light from said scintillator means and emit a responsive electrical signal, and
    fiber optic coupling means operatively associated with said scintillator means and said solid-state detector means for delivering light emitted by said scintillator means with substantial continuity to said array of solid-state detector means.

2. The stereoscopic radiography apparatus of claim 1 wherein said solid-state detector means include at least one self-scanning photodiode array.

3. The stereoscopic radiography apparatus of claim 2 including
said collimator means having at least one opening for each said beam to control the output of radiation in said beam impinging on said object.

4. The stereoscopic radiography apparatus of claim 3 including
said collimator means opening being so configurated as to provide each said beam emerging from said collimator openings as a generally fan shaped beam.

5. The stereoscopic radiography apparatus of claim 3 comprising
means for establishing relative movement between said object and said collimator means, such that portions of said object will be exposed sequentially to said radiation.

6. The stereoscopic radiography apparatus of claim 5 including
said scintillator means having at least one phosphor screen.

7. The stereoscopic radiography apparatus of claim 2 including
said self-scanning array of photodiodes being a planar array having two rows of linear self-scanning photodiode arrays disposed with said linear arrays of a first said row being staggered with respect to said linear arrays of a second said row, and
said fiber optic means alternately connecting portions of said scintillator means with a photodiode array from said first row and a photodiode array from said second row, such that adjacent portions of said scintillator means will be optically coupled to photodiode arrays in different rows.

8. The stereoscopic radiography apparatus of claim 7 including
said photodiode arrays of one said row being so positioned with respect to said photodiode arrays of the other said row that at least one transverse edge of an array of one said row will be substantially aligned with a transverse edge of an array of said other row, such that appreciable gaps and overlaps will be substantially completely eliminated and substantially continuous image information will be created.

9. The stereoscopic radiography apparatus of claim 8 including
a radiation opaque housing surrounding said scintillator means, optical coupling means and self-scanning photodiode arrays, and
said housing having an opening generally aligned with said scintillator means.

10. The stereoscopic radiography apparatus of claim 2 wherein
said self-scanning array of photodiodes includes a linear array of about 60 to 4096 photodiodes per integrated circuit.

11. The stereoscopic radiography apparatus of claim 10 including
said self-scanning array of photodiodes includes more than one linear array of self-scanning of photodiodes and said arrays being oriented generally parallel with respect to each other.

12. The stereoscopic radiography apparatus of claim 11 including
said fibers being tapered.

13. The stereoscopic radiography apparatus of claim 1 including
said signal receiving means includes digital computer means for modifying said electrical signals received from said self-scanning array of photodiodes to enhance portions of the image produced.

14. The stereoscopic radiography apparatus of claim 13 including
visual display means operatively associated with said digital computer to display said enhanced image.

15. The stereoscopic radiography apparatus of claim 3 including
said fiber optic means having a greater area of contact with said phosphor screen than with said self-scanning array of photodiodes.

16. The stereoscopic radiography apparatus of claim 15 including
some of the fibers in said fiber optic means having greater length than other fibers in said fiber optic means.

17. The stereoscopic radiography apparatus of claim 5 including
said stereoscopic imaging means having means for alternately energizing said radiation source means so that said first and said second radiation beams will be emitted in alternating fashion.

18. The stereoscopic radiography apparatus of claim 17 including
said self-scanning array of photodiodes alternately receiving light emitted by said scintillator means responsive to radiation received from said first radiation beam and said second radiation beam and passing through said object.

19. The stereoscopic radiography apparatus of claim 15 wherein
said fiber optic means taper toward said array of photodiodes.

20. The stereoscopic radiography apparatus of claim 6 including
said scintillator means having two phosphor screens with each screen adapted to receive radiation from a different said beam,
said fiber optic means having two arrays with one associated with said each phosphor screen,
two said self-scanning photodiode arrays each associated with one said fiber optic array, and
said stereoscopic imaging means having means for simultaneously causing said radiation source means to emit said first and second radiation beams with one said beam impinging on each said phosphor screen after passing through said object.

21. The stereoscopic radiography apparatus of claim 5 including
the source of said first radiation beam being spaced from the source of said second radiation beam by about 1 to 4 inches.

22. The stereoscopic radiography apparatus of claim 20 wherein
said first and second radiation beams are adapted to both pass through at least one common portion of said object simultaneously.

23. The stereoscopic radiography apparatus of claim 22 wherein
said common portion of said object is an elongated portion, and
said first and second radiation beams crossing at said elongated portion, such that said portion will be imaged from two different angles substantially simultaneously.

24. A method of stereoscopic radiographic imaging of an object comprising
providing a source of two radiation beams, an object to be imaged and radiation detectors,
causing said radiation beams to impinge substantially simultaneously upon said object in different paths with portions thereof passing through said object,
employing said radiation detectors to convert the portions of said radiation beams passing through said object into electrical signals containing first image information from said first beam and second image information from said second beam,
providing scintillator means and at least one self-scanning array of photodiodes as said radiation detectors,
converting radiation passing through said object into light by said scintillator means,
converting said light into electrical signals containing image information by means of said self-scanning array of photodiodes, and
passing a portion of said first beam and a portion of said second beam through a common portion of said object.

25. The method of stereoscopic radiographic imaging of claim 24 including
exposing said object to said first and second beams simultaneously.

26. The method of stereoscopic radiographic imaging of claim 24 including
exposing said object to said first and second beams sequentially.

27. The method of stereoscopic radiographic imaging of claim 26 including
causing said first and second beams to cross within said object.

* * * * *